United States Patent [19]

Tomiuga et al.

[11] Patent Number: 4,590,207

[45] Date of Patent: May 20, 1986

[54] THERAPEUTIC AND/OR PREVENTIVE OPHTHALMIC SOLUTION FOR INTRAOCULAR HYPERTENSION AND GLAUCOMA

[75] Inventors: Takashi Tomiuga, Tokorozawa; Keiichi Nomura, Houya; Tetsuya Tajima, Noda, all of Japan

[73] Assignee: Eisai Co., Ltd., Tokyo, Japan

[21] Appl. No.: 689,903

[22] Filed: Jan. 9, 1985

[30] Foreign Application Priority Data

Jan. 18, 1984 [JP] Japan .................................. 59-5663

[51] Int. Cl.⁴ ............................................. A61K 31/34
[52] U.S. Cl. ..................................... 514/470; 514/913

[58] Field of Search ................. 514/470, 913; 549/464

[56] References Cited

U.S. PATENT DOCUMENTS

| | | | |
|---|---|---|---|
| 3,342,680 | 9/1967 | Treon | 514/470 |
| 4,381,400 | 4/1983 | Emeury et al. | 549/464 |
| 4,417,065 | 11/1983 | Stoss | 549/464 |
| 4,431,830 | 2/1984 | Schönafinger | 549/464 |

*Primary Examiner*—Douglas W. Robinson
*Attorney, Agent, or Firm*—Flynn, Thiel, Boutell & Tanis

[57] ABSTRACT

Therapeutic and/or preventive ophthalmic solution for intraocular hypertension and glaucoma contains isosorbide mononitrate as an active ingredient.

7 Claims, No Drawings

THERAPEUTIC AND/OR PREVENTIVE OPHTHALMIC SOLUTION FOR INTRAOCULAR HYPERTENSION AND GLAUCOMA

This invention relates to a therapeutic and/or preventive ophthalmic solution for intraocular hypertension and glaucoma. More particularly, it relates to a therapeutic and/or preventive ophthalmic solution for intraocular hypertension and glaucoma containing isosorbide mononitrate as an active ingredient for treating and/or preventing intraocular hypertension and glaucoma.

Glaucoma is a difficulty curable disease wherein a continuous increase in intraocular tension would result in optic functional disorders or anatomic changes in the bulbus oculi. It is an object of the medicinal therapy for glaucoma to maintain normal intraocular tension to thereby avoid the optic functional disorders.

Conventional methods for controlling intraocular tension include oral administration or intravenous or intramuscular injection of carbonic anhydrase inhibitors, drip of hypertonic osmotic agents such as mannitol or glycerol and instillation of pilocarpine and epinephrine. Although instillation of a β-blocker has also been performed recently, the curative power and the control of side effects thereof is still insufficient.

Under these circumstances, we have tried to develop a novel therapeutic and/or preventive drug for glaucoma for a long time and have found unexpectedly that an ophthalmic solution containing isosorbide mononitrate as an active ingredient is effective in treating and/or preventing intraocular hypertension and. We have thereby completed the present invention.

Accordingly the present invention provides an effective therapeutic and/or preventive drug for intraocular hypertension and glaucoma caused by persistent intraocular hypertension.

Isosorbide nitrate may be classified into two types, i.e. isosorbide dinitrate and isosorbide mononitrate.

The former, i.e. isosorbide dinitrate, of the following structure:

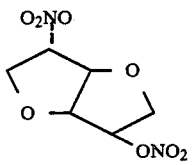

(I)

has been used in treating and/or preventing stenocardia, myocardial infarction and coronary sclerosis.

On the other hand, the latter, i.e. isosorbide mononitrate, is a mononitro compound having two isomeric forms as shown below.

(1) isosorbide-2-mononitrate

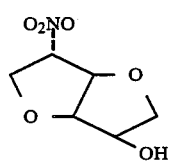

(II)

(2) isosorbide-5-mononitrate

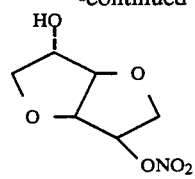

(III)

Isosorbide dinitrate and nitroglycerin have been frequently used in the treatment of patients suffering from stenocardia which is a geriatric disease. However these compounds have been considered to be contraindicated for these patients with glaucoma.

As a result of our prolonged researches to develop a safe ophthalmic solution for treating and/or preventing intraocular hypertension and glaucoma, we have found that an aqueous ophthalmic solution, or eye drops, containing isosorbide mononitrate would be an effective therapeutic and/or preventive drug for glaucoma because of its unexpected effect of lowering intraocular tension.

We have further found that the abovementioned isosorbide dinitrate (I) would also lower intraocular tension. However it is necessary to employ an oily solvent to dissolve the compound (I) to give an effective concentration. The oily ophthalmic solution thus prepared is undesirable since its use might give a patient local discomfort. In addition, oily solvents presently available are unstable and form irritating substances during storage so that their use is limited.

On the contrary, isosorbide-2-mononitrate (II) and isosorbide-5-mononitrate (III) of the present invention are highly soluble in water and can maintain an effective concentration in an aqueous solvent, thereby giving no discomfort to a patient. Accordingly these compounds are very desirable as therapeutic and/or preventive drugs for glaucoma.

Ophthalmic solution are prepared from isosorbide mononitrate, i.e. isosorbide-2-mononitrate (II) or isosorbide-5-mononitrate (III) in a conventional manner.

More particularly, said compound is dissolved in a solvent such as sterilized distilled water or a physiological saline solution and additives such as an isotonic agent, pH regulator, various preservatives and stabilizers are added thereto, if necessary, to give an ophthalmic solution.

The ophthalmic solution is used by portions over a prolonged period so that various preservatives such as methyl p-hydroxybenzoate, ethyl p-hydroxybenzoate, propyl p-hydroxybenzoate, butyl p-hydroxybenzoate, chlorobutanol, benzalconium chloride and thimerosal are frequently employed.

Typical formulations of the ophthalmic solution are as follows.

| Formulation 1: 0.3% ophthalmic solution | | |
|---|---|---|
| isosorbide-5-mononitrate | | 0.3 g |
| boric acid | | 2.0 g |
| distilled water | g.s. | to 100.0 ml |
| Formulation 2: 3% ophthalmic solution | | |
| isosorbide-2-mononitrate | | 3.0 g |
| benzalconium chloride | | 0.03 g |
| antiseptic water | g.s. | to 100.0 ml |

Ophthalmic solution can be prepared in a conventional manner by using each formulation as shown above.

The effective dose of the isosorbide mononitrate of the present invention depends on various factors including the symptom and age of a patient. Usually one or two drops of a 0.1 to 5% solution is administered once to an adult patient, though not limited thereto.

The ophthalmic solution of the present invention should be administered continuously to treat and/or prevent glaucoma. Thus the high safety of the isosorbide mononitrate makes the present invention more valuable.

Now the result of a toxicity test will be given.

EXPERIMENTAL EXAMPLE 1: Acute toxicity 500 mg/kg and 1,000 mg/kg of each of isosorbide-5-mononitrate (5-ISMN) and isosorbide-2-mononitrate (2-ISMN) were intravenously injected to ddy mice of approximately 20 g in body weight to observe their toxicity. The mortality was determined 24 hours after the administration.

Slight ataxia and restlessness were observed in the animals to which was administered 500 mg/kg of 5-ISMN although these symptoms disappeared within 30 min. No animal died of the ten animals in this group. Furthermore no animal died in the group to which was administered 1,000 mg/kg of 5-ISMN.

No animal died of the ten animals in both of the groups to which were administered 500 mg/kg and 1,000 mg/kg of 2-ISMN, respectively. Slight ataxia was also observed in these groups.

To further illustrate the effect of the present invention, an experimental example will be given.

EXPERIMENTAL EXAMPLE 2: Effect on intraocular hypertension of rabbits caused by α-chymotrypsin (1) Method Models of intraocular hypertension were prepared by the use of male white rabbits of approximately 2.5 kg in body weight according to the method reported by Sears (cf. Sears, D. and Sears, M., Am. J. Ophthalmol., Vol. 77, No. 3, p. 378 to 383, 1974). A rabbit was anesthetized by intravenously injecting 20 mg/kg of pentobarbital sodium and 2% of lidocaine was instilled in the left eye of the animal to anesthetize locally. A volume of 0.5 ml physiological saline solution was injected into the anterior chamber of the left eye with a needle and subsequently 0.5 ml of α-chymotrypsin 300 NFU/ml was injected into the posterior chamber with another needle while holding the former needle as such. After removing the needle inserted into the posterior chamber, the needle inserted into the anterior chamber was removed.

The rabbit experimentally suffering from intraocular hypertension thus prepared was allowed to stand for 25 to 30 days to thereby recover from postoperative keratitis or conjunctivitis and to hold a stable intraocular hypertension. Then it was subjected to the test.

Intraocular tension was determined with a Perkin's Hand Applanation Tonometer (a product of Clement Clark, London) under anesthesia with 2% halothane, having 2 l/min of oxygen, and local anesthesia with 0.4% of benoxil.

Intraocular tension was measured five times and the mean value was recorded.

5-ISMN and 2-ISMN were employed as the test compounds and dissolved in a physiological saline solution.

A volume of 35 μl of each solution was instilled in the left eye treated with α-chymotrypsin. Each solution was administered to five rabbits according to a crossover design.

(2) Results

Results are shown in Table 1.

TABLE 1

| Compound | Intraocular tension | | | | | |
|---|---|---|---|---|---|---|
| | 0 hr | 1 hr | 3 hr | 5 hr | 7 hr | 9 hr |
| Physiological saline solution 0.9% | 30.2 ± 0.2 | 30.7 ± 0.4 | 29.5 ± 0.4 | 29.9 ± 0.6 | 30.3 ± 0.2 | 30.9 ± 0.4 |
| 2-ISMN 3.0% | 31.2 ± 0.6 | 29.0 ± 0.8 | 29.1 ± 0.9 | 25.1 ± 1.4* | 24.6 ± 1.4** | 21.8 ± 1.3** |
| 5-ISMN 0.3% | 30.5 ± 0.8 | 21.5 ± 0.5** | 20.1 ± 0.9** | 19.8 ± 1.2** | 20.5 ± 0.7** | 19.6 ± 1.8** |
| 5-ISMN 1.0% | 30.2 ± 0.5 | 22.0 ± 1.9** | 19.1 ± 0.6** | 18.6 ± 0.9** | 18.5 ± 1.0** | 19.8 ± 1.3** |
| 5-ISMN 3.0% | 30.8 ± 0.8 | 20.3 ± 0.9** | 16.4 ± 0.5** | 15.7 ± 0.5** | 16.2 ± 1.8** | 16.2 ± 2.2** |

Note:
Intraocular tension is represented by the mean value of five animals ± standard error
*$p < 0.05$,
**$p < 0.01$ (calibrated by t calibration with the use of the group to which was administered the physiological saline solutions as a control).

Table 1 of Experimental Example 2 obviously indicates that 5-ISMN of the present invention exhibits a remarkable effect of lowering intraocular tension when administered in a dose of 0.3 to 3%. This effect would depend on the dose and continue for at least nine hours. On the other hand, 2-ISMN exhibits an effect of lowering intraocular tension when administered in a dose of 3%.

Accordingly the ophthalmic solution of the present invention containing 5-ISMN or 2-ISMN exhibit remarkable, continuous effects of lowering intraocular tension and so are useful as therapeutic and/or preventive drugs for intraocular hypertension and glaucoma.

The embodiments of the invention in which an exclusive property or privilege is claimed are defined as follows:

1. A method of treating glaucoma and intraocular hypertension which comprises instilling into the eye of a patient requiring such treatment, an ophthalmic solution comprising a pharmaceutically acceptable carrier liquid and an amount of isosorbide mononitrate sufficient to reduce intraocular pressure.

2. A method as claimed in claim 1, in which said isosorbide mononitrate is isosorbide-2-mononitrate.

3. A method as claimed in claim 1, in which said isosorbide mononitrate is isosorbide-5-mononitrate.

4. A method as claimed in claim 1, in which said carrier liquid is distilled water or physiological saline.

5. A method as claimed in claim 1, in which said ophthalmic solution contains from 0.1 to 5 wt. % of said isosorbide mononitrate.

6. A method as claimed in claim 2, in which said ophthalmic solution contains about 3.0 wt. % of said isosorbide-2-mononitrate.

7. A method as claimed in claim 3, in which said ophthalmic solution contains from about 0.3 to about 3.0 wt. % of isosorbide-5-mononitrate.

* * * * *